United States Patent
Tonmukayakul et al.

(10) Patent No.: US 7,992,427 B2
(45) Date of Patent: Aug. 9, 2011

(54) DEVICE AND METHOD FOR TESTING FRICTION REDUCTION EFFICIENCY AND SUSPENSION SYSTEMS

(75) Inventors: Narongsak Tonmukayakul, Duncan, OK (US); Jason Bryant, Duncan, OK (US); Robert Pipkin, Marlo, OK (US)

(73) Assignee: Halliburton Energy Services Inc., Duncan, OK (US)

( * ) Notice: Subject to any disclaimer, the term of this patent is extended or adjusted under 35 U.S.C. 154(b) by 486 days.

(21) Appl. No.: 12/166,992

(22) Filed: Jul. 2, 2008

(65) Prior Publication Data
US 2010/0004890 A1 Jan. 7, 2010

(51) Int. Cl.
*G01N 11/14* (2006.01)

(52) U.S. Cl. ............ 73/54.28; 73/54.32; 73/54.35; 73/54.38

(58) Field of Classification Search .......... 73/54.02, 73/54.28, 54.32, 54.33, 54.35, 54.38
See application file for complete search history.

(56) References Cited

U.S. PATENT DOCUMENTS

| | | |
|---|---|---|
| 2,626,786 A | 1/1953 | McGlothlin |
| 2,846,873 A | 8/1958 | Källe |
| 3,269,171 A | 8/1966 | Bruss et al. |
| 4,283,938 A | 8/1981 | Epper et al. |
| 4,468,953 A | 9/1984 | Garritano |
| 4,524,611 A * | 6/1985 | Richon et al. ............ 73/54.35 |
| 4,557,142 A | 12/1985 | Hensley et al. |
| 4,612,800 A * | 9/1986 | Erian ...................... 73/54.01 |
| 4,653,313 A | 3/1987 | Sabins et al. |
| 4,829,811 A * | 5/1989 | Ehlert et al. ............ 73/54.35 |
| 5,042,292 A | 8/1991 | Plint et al. |
| 5,708,197 A | 1/1998 | Todd et al. |
| 5,799,734 A | 9/1998 | Norman et al. |
| 6,055,874 A | 5/2000 | Onan et al. |
| 6,257,051 B1 | 7/2001 | Boyle et al. |
| 6,584,833 B1 | 7/2003 | Jamison et al. |
| 6,629,451 B1 | 10/2003 | Taylor |

(Continued)

FOREIGN PATENT DOCUMENTS

EP  0399634 A2  11/1990

(Continued)

OTHER PUBLICATIONS

Torgeir Nakken, et al., Measurements of polymer induced drag reduction and polymer scission in Taylor flow using standard double-gap sample holders with axial symmetry, Journal of Non-Newtonian Fluid Mechanics, 2001, pp. 1-12.

(Continued)

*Primary Examiner* — Daniel Larkin
(74) *Attorney, Agent, or Firm* — John W. Wustenberg; Conley Rose, P.C.

(57) ABSTRACT

Methods and devices for testing friction reduction systems are described herein. Embodiments of the disclosed devices allow direct measurement of fluid or rheological properties of friction reduction systems in a "one pot" or integrated device while maintaining the particles in suspension. In an embodiment, a device for testing a friction reduction system comprises an outer chamber. The device also comprises an impeller disposed at the bottom of the outer chamber for mixing the friction reduction system. In addition, the device comprises an inner chamber fixedly disposed within the outer chamber. The inner chamber has an inlet and an outlet such that the inner chamber is in fluid communication with the outer chamber. The device further comprises a bob rotatably disposed within the inner chamber.

15 Claims, 6 Drawing Sheets

U.S. PATENT DOCUMENTS

| | | | |
|---|---|---|---|
| 6,755,079 | B1 | 6/2004 | Proett et al. |
| 6,782,735 | B2 | 8/2004 | Walters et al. |
| 6,874,353 | B2 | 4/2005 | Johnson et al. |
| 6,997,045 | B2 | 2/2006 | Wallevik et al. |
| 7,079,244 | B2 | 7/2006 | Gold et al. |
| 7,392,842 | B2 | 7/2008 | Morgan et al. |
| 7,712,526 | B2 | 5/2010 | Morgan et al. |
| 2003/0056575 | A1* | 3/2003 | Hettwer et al. ............. 73/54.28 |
| 2004/0126874 | A1 | 7/2004 | Sakai et al. |
| 2008/0047328 | A1 | 2/2008 | Wang |
| 2008/0062212 | A1 | 3/2008 | Na |
| 2008/0105040 | A1* | 5/2008 | Bivens et al. ............... 73/54.28 |

FOREIGN PATENT DOCUMENTS

| | | |
|---|---|---|
| EP | 1712890 A2 | 10/2006 |
| GB | 2188162 A | 9/1987 |

OTHER PUBLICATIONS

Ancey, Christophe, "Solving the Couette inverse problem using a wavelet-vaguelette decompositon," J. Rheol., Mar./Apr. 2005, pp. 441-460, vol. 49, No. 2, The Society of Rheology, Inc.

Bird, R. Byron, et al., "Transport phenomena," Second Edition, Jul. 2001, 1 cover page and 1 figure, John Wiley & Sons Inc.

Brady, John F., et al., "Microstructure of strongly sheared suspensions and its impact on rheology and diffusion," J. Fluid Mech., 1997, pp. 103-139, vol. 348, Cambridge University Press, United Kingdom.

Clarke, B., "Rheology of coarse settling suspensions," 1967, pp. T251 to T256, vol. 45, Trans. Instn Chem. Engrs.

Krieger, Irvin M., "Rheology of monodisperse latices," Advances in Colloid and Interface Science, 1972, pp. 111-136, vol. 3, Elsevier Publishing Company, The Netherlands.

Lord, D. L., "Helical screw rheometer: a new tool for stimulation fluid evaluation," SPE 18213, 63rd Annual Technical Conference and Exhibition of the Society of Petroleum Engineers, Houston, Texas, Oct. 2-5, 1988, 7 pages, Society of Petroleum Engineers.

Lord, D. L., et al., "Real-time fracturing fluid rheology measurements with the helical screw rheometer," SPE 19734, 64th Annual Technical Conference and Exhibition of the Society of Petroleum Engineers, San Antonio, Texas, Oct. 8-11, 1989, pp. 321-328, Society of Petroleum Engineers.

Morris, J. F., et al., "Pressure-driven flow of a suspension: buoyancy effects," Int. J. Multiphase Flow, 1998, pp. 105-130, vol. 24, No. 1, Elsevier Science Ltd., Great Britain.

Morris, Jeffrey F., et al., "Curvilinear flows of noncolloidal suspensions: the role of normal stresses," J. Rheol., Sep./Oct. 1999, pp. 1213-1237, vol. 43, No. 5, The Society of Rheology, Inc.

Nguyen, Q. D., et al., "Characterization of yield stress fluids with concentric cylinder viscometers," 1987, pp. 508-515, vol. 26, No. 6, Rheologica Acta.

Nguyen, Q. D., et al., "Measuring the flow properties of yield stress fluids," Annu. Rev. Fluid Mech., 1992, pp. 47-88, vol. 24, Annual Reviews Inc.

Patent application entitled "Flow-through apparatus for testing particle laden fluids and methods of making and using same," by Narongsak Tonmukayakul, et al., filed Jul. 28, 2008, as U.S. Appl. No. 12/180,668.

Saraf, D. N., et al., "Some studies on the viscosity of settling suspensions," Aug. 1975, pp. 449-452, vol. 53, The Canadian Journal of Chemical Engineering.

Sparrow, E. M., et al., "Instability of the flow between rotating cylinders: the wide-gap problem," 1964, pp. 35-46, vol. 20, Part 1, J. Fluid Mech., Great Britain.

Stickel, Jonathan J., et al., "Fluid mechanics and rheology of dense suspensions," Annu. Rev. Fluid Mech., 2005, pp. 129-149, vol. 37, Annual Reviews.

Thesing, A., "New device for rheology measurements of proppant-laden fluids with the Fann 50 viscometer," SPE 58759, SPE International Symposium on Formation Damage Control, Lafayette, Louisiana, Feb. 23-24, 2000, pp. 1-10, Society of Petroleum Engineers.

Yeow, Y. Leong, "Solving the inverse problem of Couette viscometry by Tikhonov regularization," J. Rheol., Nov./Dec. 2000, pp. 1335-1351, vol. 44, No. 6, The Society of Rheology, Inc.

Foreign communication from a related counterpart application—International Search Report and Written Opinion, PCT/GB2009/001654, Sep. 18, 2009, 12 pages.

Foreign communication from a related counterpart application—International Preliminary Report on Patentability, PCT/GB2009/001654, Feb. 1, 2011, 8 pages.

* cited by examiner

DEVICE AND METHOD FOR TESTING FRICTION REDUCTION EFFICIENCY AND SUSPENSION SYSTEMS

CROSS-REFERENCE TO RELATED APPLICATIONS

The subject matter of the present application is related to U.S. patent application Ser. No. 11/246,816 filed Oct. 7, 2005, now U.S. Pat. No. 7,392,842, and entitled "Proppant Suspension Testing Devices and Methods of Use," which is hereby incorporated herein by reference in their entirety for all purposes.

STATEMENT REGARDING FEDERALLY SPONSORED RESEARCH OR DEVELOPMENT

Not applicable

BACKGROUND

1. Field of the Invention

This invention relates generally to the field of rheometry. More specifically, the invention relates to a method and device for testing friction reduction systems.

2. Background of the Invention

Various industries such as the oil industry may need to test the efficiency of friction reduction agents or systems to determine if they are suitable for their intended use. To date, examining the efficiency of friction reduction agents typically involves measuring pressure drop in a pipe at a given flow rate and correlating the difference in pressure drop to friction reduction efficiency. This technique may be satisfactory for large scale or high Reynolds number measurements, but requires a substantial amount of sample for each test. The major disadvantages of the flow loop technique make this technique unsuitable for measuring efficiency of a friction reduction agent at the fracturing location, which is a primary situation of interest. Thus, development of a simple, reliable and mobile device and technique that can directly test a friction reducer is urgently required.

Furthermore, particulate matter in particle laden systems has a tendency to settle during an experiment and thus, an inaccurate measurement may result. Conventional rheometers do not take into account this settling effect in particle laden systems nor do they maintain particle laden system in suspension. Accordingly, reliable testing of the effect of these stress-reducing and/or friction reducing techniques has been problematic due to the fact that existing rheometers have been unable to measure, with the desired accuracy needed, the stress and strain of a material having a high concentration of solids or particles.

Consequently, there is a need for improved methods and devices for suspension testing of particle laden systems.

BRIEF SUMMARY

Methods and devices for testing friction reduction systems and/or particle laden systems are described herein. Embodiments of the disclosed devices allow direct measurement of fluid or rheological properties of friction reduction systems in a "one pot" or integrated device. The disclosed methods and devices may also be used to directly measure onset of flow stability in fluid systems. In addition, embodiments of the disclosed device provide a "one pot" solution of conducting friction reducing experiments. Further advantages and features of the disclosed device are described in more detail below.

In an embodiment, a device for testing a friction reduction system comprises an outer chamber. The device also comprises an impeller disposed at the bottom of the outer chamber for mixing the friction reduction system. In addition, the device comprises an inner chamber fixedly disposed within the outer chamber. The inner chamber has an inlet and an outlet such that the inner chamber is in fluid communication with the outer chamber. The device further comprises a bob rotatably disposed within the inner chamber.

In another embodiment, a method of determining one or more bulk rheological properties of friction reduction system comprises providing a device comprising an outer chamber, an impeller disposed at the bottom of the outer chamber, an inner chamber disposed within the outer chamber and in fluid communication with the outer chamber, and a rotatable bob disposed within the inner chamber, The method further comprises loading the friction reduction system into the outer chamber of the device. Additionally, the method comprises simultaneously mixing the friction reduction system with the impeller so as to circulate the friction reduction system into the inner chamber and shearing the friction reduction system with the bob as the friction reduction system flows from the outer chamber to the inner chamber. Moreover, the method comprises collecting torque data from the impeller and the bob to determine one or more bulk rheological properties of the friction reduction system.

In yet another embodiment, a method of determining onset of instability in a friction reduction system comprises providing a device comprising an outer chamber, an impeller disposed at the bottom of the outer chamber, an inner chamber disposed within the outer chamber and in fluid communication with the outer chamber, and a rotatable bob disposed within the inner chamber. The method additionally comprises loading the friction reduction system into the outer chamber of the device. Furthermore, the method comprises shearing the friction reduction system with the impeller so as to circulate the friction reduction system into the inner chamber. The method also comprises halting rotation of the impeller and shearing the friction reduction system with the bob as the friction reduction system flows from the outer chamber to the inner chamber. In addition, the method comprises decreasing the rotational speed of the bob over time while collecting torque data from the bob to determine onset of instability in a friction reduction system.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct connection, or through an indirect connection via other devices and connections.

DETAILED DESCRIPTION OF THE PREFERRED EMBODIMENTS

Figure 1:
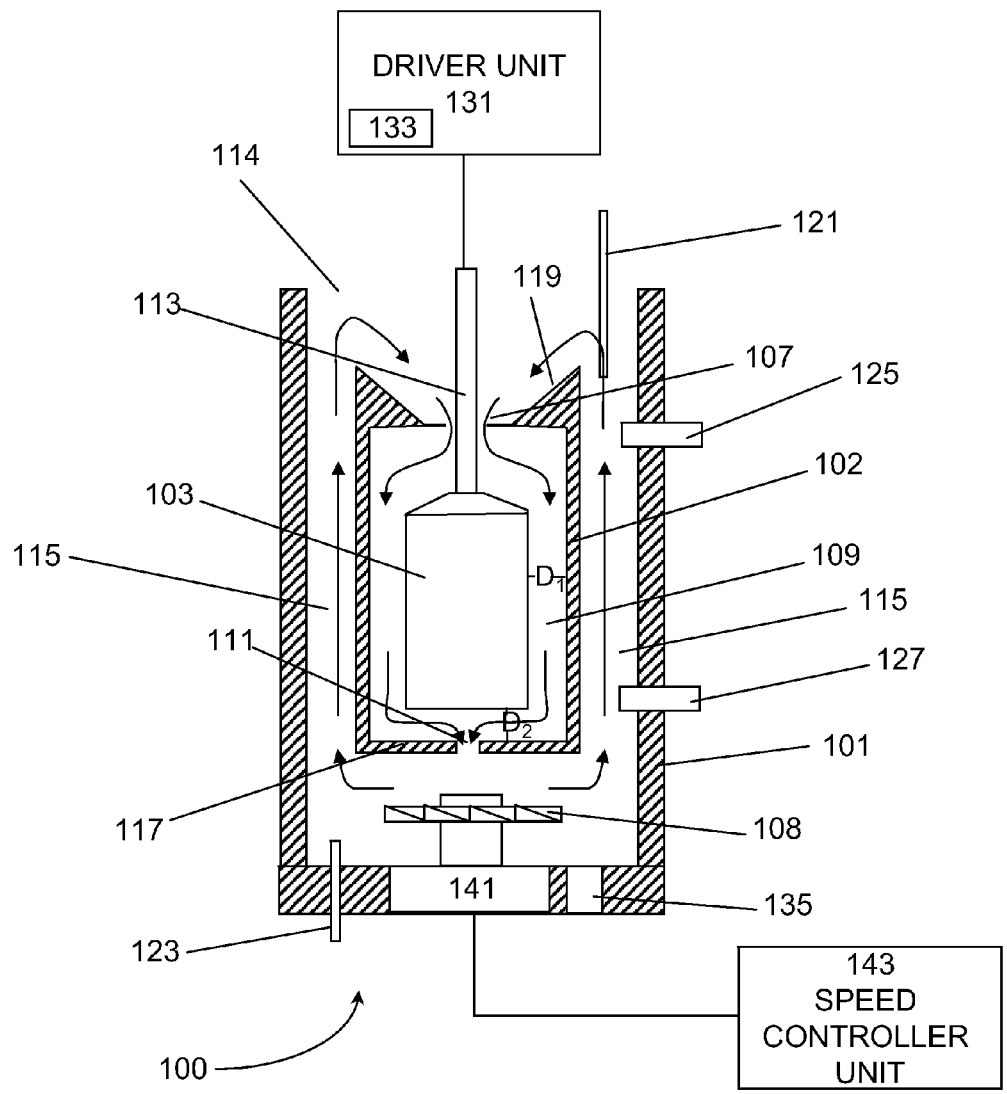
FIG. 1 illustrates a cross-sectional schematic of an embodiment of a device for testing friction reduction systems.

FIG. 1 illustrates an embodiment of a device or rheometer 100 for testing of friction reduction systems. As used herein, the term "friction reduction system(s)" may refer to any mixture, suspension, solution, or fluid containing compounds or agents used for reducing friction. Additionally, friction reduction systems may include "particle laden systems" which may refer to any mixture, suspension, solution, or fluid containing particulate matter (e.g., suspended solids). The term "rheometer" encompasses testing devices for testing at multiple and/or single speeds, multiple and/or single frequencies, stresses, and strains, for obtaining rheological properties of fluids. Device 100 generally includes an inner chamber 102, an outer chamber 101, and a bob 103. The device 100 also includes an impeller 108 for mixing test samples in the outer hollow chamber 101 and maintaining suspension of particulate matter in the test sample. Impeller 108 further circulates the friction reduction system up through circulating gaps 115 to inlet 107 of inner chamber 102.

Inner hollow chamber 102 is disposed within outer chamber 101 while bob 103 is disposed within inner chamber 102 and suspended from shaft 113. Inner chamber 102 has an inlet 107 located at the top portion of inner chamber 102. Inlet 107 allows inner chamber 102 to be in fluid connection with outer chamber 101. Samples from outer chamber 101 flow into inner chamber 102 through inlet 107 from the annular space or circulating gap 115 formed between inner chamber 102 and outer chamber 101. The ratio of inner diameter of outer chamber 101 to the outer diameter of inner chamber 102 may range from about 1.2 to about 5, alternatively from about 1.3 to about 3, alternatively from about 1.5 to about 2.

Outer chamber 101 generally may be cylindrical in geometry. However, outer chamber 101 may be configured with any suitable cross-sectional geometry (e.g., circle, oval, ellipse, square, etc.). Impeller 108 is preferably centrally disposed adjacent (e.g., near, at, proximate) the bottom of the inner volume of outer chamber 101 in such a way (e.g., with one or more seals) as to prevent fluid leakage from outer chamber 101. Outer chamber 101 further has an opening 114 at the top of outer chamber 101 for adding the test sample into device 100. The opening 114 may be further defined by a lid or topper having a closable or sealable opening (e.g., cap), and such lid may provide for a sealed device that may be pressured up during testing, for example via addition of heat to the sample. in some embodiments, outer chamber 101 may have a drain valve located at the bottom of outer chamber 101 to remove a test sample, once testing is completed.

Figure 3:
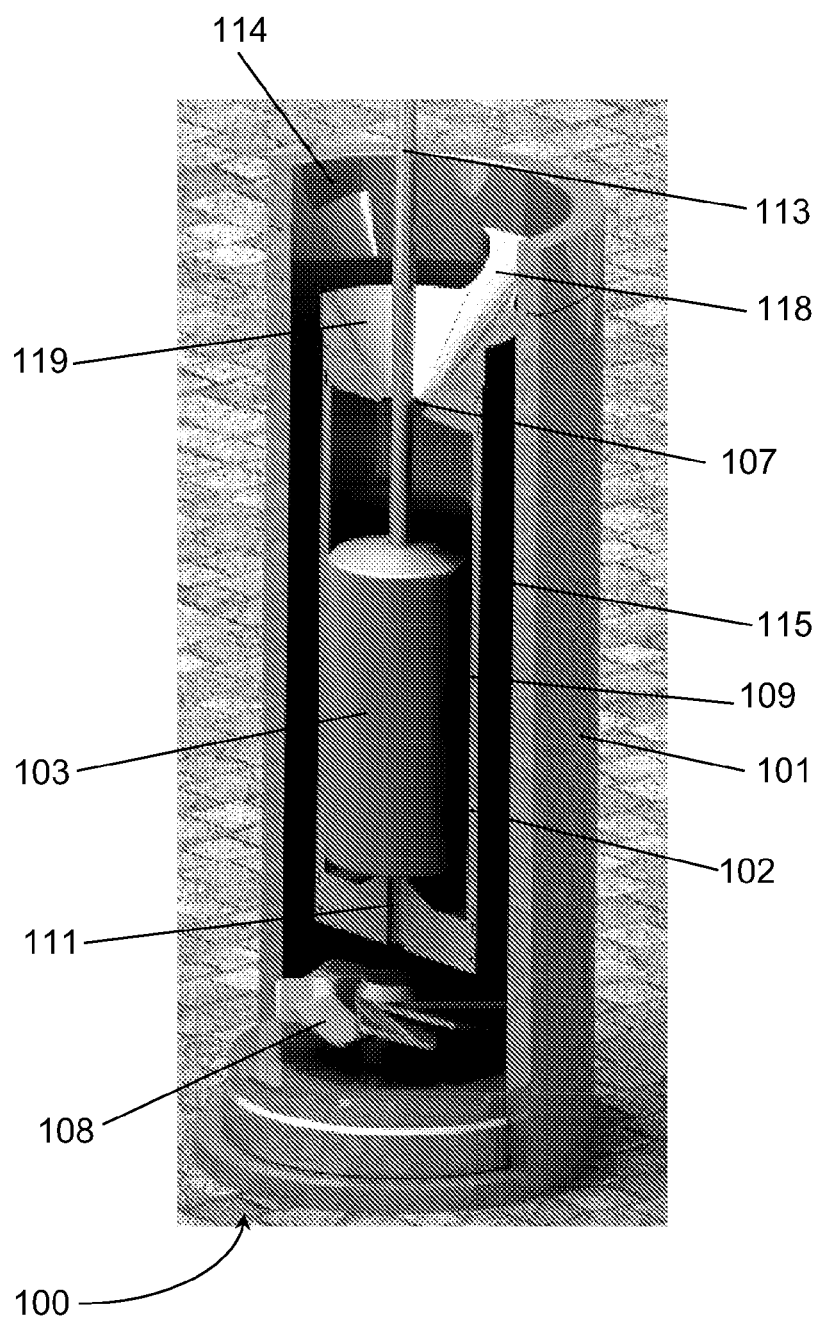
FIG. 3 illustrates a perspective rendering of an embodiment of a device for testing friction reduction systems.

Inner chamber 102 is disposed within the interior volume of outer hollow chamber 101. Furthermore, inner chamber 102 may be fixedly disposed within the interior volume of the outer chamber. That is, although bob 103 and impeller 108 may rotate, inner chamber 102 remains stationary, provided however that inner chamber 102 may further be removable from the interior volume of the outer hollow chamber for disassembly, storage, transport, cleaning, etc. Inner hollow chamber 102 may be fixed within outer chamber 101 via coupling members (e.g., ribs) spanning the annular circulating gap 115 between inner surface of the outer chamber 101 and outer surface of inner chamber 102. Alternatively, inner chamber 102 may be affixed to outer chamber 101 via an extension 118 of inlet 107 as shown in FIG. 3. Such connections (e.g., extensions 118 or annular ribs) may be releasable in nature, for example sliding or matting with corresponding or mating structures (e.g., tongue and groove) and may further be lockable in place (e.g., rotate and lock). Inner chamber 102 may have the same or different geometry as outer chamber 101. For example, inner chamber 102 may be a sleeve or cylinder that houses bob 103. Preferably, both inner chamber 102 and outer hollow chamber 101 are cylindrical in geometry such that inner hollow chamber 102 is coaxially or concentrically disposed within outer hollow chamber 101, In an embodiment, inlet 107 of inner chamber 102 may have an inverted frusto-conical surface 119 so as to guide or channel flow of the test sample into annular gap (e.g., measuring gap 109) of inner chamber 102. In other words, inlet 107 may be funnel-shaped to guide a fluid sample into inner chamber 102. A portion 118 of inlet 107 may be raised and coupled to inner surface of outer chamber 101 as shown in FIG. 3.

Although bob 103 may be configured in any shape or geometry, bob 103 is preferably cylindrical. The distance, $D_1$, between the outer surface of bob 103 and inner surface of inner chamber 102 may be referred to as the measuring gap 109. The ratio of the inner diameter of inner chamber 102 to the outer diameter of bob 103 may range from about 1.2 to about 5, alternatively from about 1.3 to about 3, alternatively from about 1.5 to about 2. Preferably, measuring gap 109 has a distance at least about ten times the average diameter of the particles in the sample. Furthermore, the distance, $D_2$, between the bottom of bob 103 and the bottom inner surface of inner chamber 102 may be any suitable distance. However, $D_2$ preferably has a distance substantially equal to the diameter of bob 103.

Furthermore, bob 103 may be coupled to shaft 113, which in turn may be coupled to a driver unit 131 (e.g., motor) for rotating bob 103. Accordingly, bob 103 rotates within inner chamber 102 via shaft 113 and driver unit 131. The driver unit 131 may be any known means for rotating bob such as without limitation, engines, mixers, motors, etc. Moreover, in some embodiments, bob 103 may be removable from inner chamber 102 and interchangeable such that different sized and/or shaped bobs may be used to adjust the distance, $D_1$, of the annular gap 109 and/or distance from the bottom of the bob, $D_2$. Driver unit 131 may incorporate a torque sensor 133 for measuring the force of the sample exerted on bob 103.

One or more outlets 111 may be disposed at the bottom 117 of inner chamber 102 so as to allow the test sample to flow out of the inner chamber 102 and back into outer chamber 101. Inlet 107 and outlet 111 provide fluid communication between inner chamber 102 and outer chamber 101 and allow recirculation of fluid between the chambers. The outlets may be of any suitable shape and may be located at any suitable location. In an embodiment, a single circular outlet 111 is located at about the center of the bottom of inner chamber 102 (e.g., a radius of the outlet 111 and a radius of the inner chamber 102 share a common or about common center point). In embodiments where outlet 111 is circular, it may have any suitable diameter. Preferably, outlet 111 has a diameter substantially the same as distance, $D_1$ (i.e. measuring gap 109).

Impeller 108 may be any impeller known to those of ordinary skill in the art. Examples of suitable impellers include without limitation, propellers, multi-blade impellers, helical impellers, turbines, axial flow impellers, radial flow impellers, vortex impellers, and the like. In addition, impeller 108 may he open, semi-open, or closed. Furthermore, impeller 108 may be made from metal, polymer, alloys, or combinations thereof, Impeller 108 is generally coupled to a motor 141 for rotating impeller 108 at a given rotational speed. Motor 141 may be external to device 100 or alternatively, may be housed adjacent or in the bottom of outer chamber 101 as shown in FIG. 1. Additionally, motor 141 may have a torque sensor to measure torque being applied to impeller 108 from a sample. A speed controller unit 143 coupled to motor 141 may be used to control rotational speed of impeller 108. Motor 141 may be directly coupled (e.g., via a shaft or gears) or indirectly coupled (e.g., inductive or magnetic coupling) to the motor 141. Where needed, various seals (e.g., O-rings) and bearings may be used in a drive train connecting impeller 108 and motor 141 such that a leak-proof seal is formed in any openings in the bottom of outer chamber 101. The motor 141 may be coupled to a torque sensor to measure torque on impeller 108.

A plurality of sensors may be used to measure various properties at different areas of device 100. The sensors may be used to measure pressure, temperature, differential pressure, or combinations thereof. In particular, a temperature sensor 121 may be disposed adjacent the top or upper portion of outer chamber 101. Another temperature sensor 123 may be disposed adjacent the bottom or lower portion of outer chamber 101, e.g., adjacent to impeller 108. Temperature sensors may be any devices known to those of skill in the art capable of measuring temperature such as without limitation, thermocouples, thermometers, etc. The temperature sensors may be positioned within the device 100 such that one or more sensors are in contact with and/or measure the temperature of a test sample in the device. Moreover, pressure sensors or transducers 125, 127 may be placed adjacent the upper and lower portions of outer chamber 101 to determine a pressure drop from the top to the bottom of outer chamber 101.

In an embodiment, the device 100 may be equipped with a heater and/or cooler to control the temperature of the sample. For example, a heating and/or cooling coil or jacket may be disposed interior and/or exterior to the outer chamber 101. Alternatively, the device 100 may be immersed in a heating or cooling bath.

Figure 2:
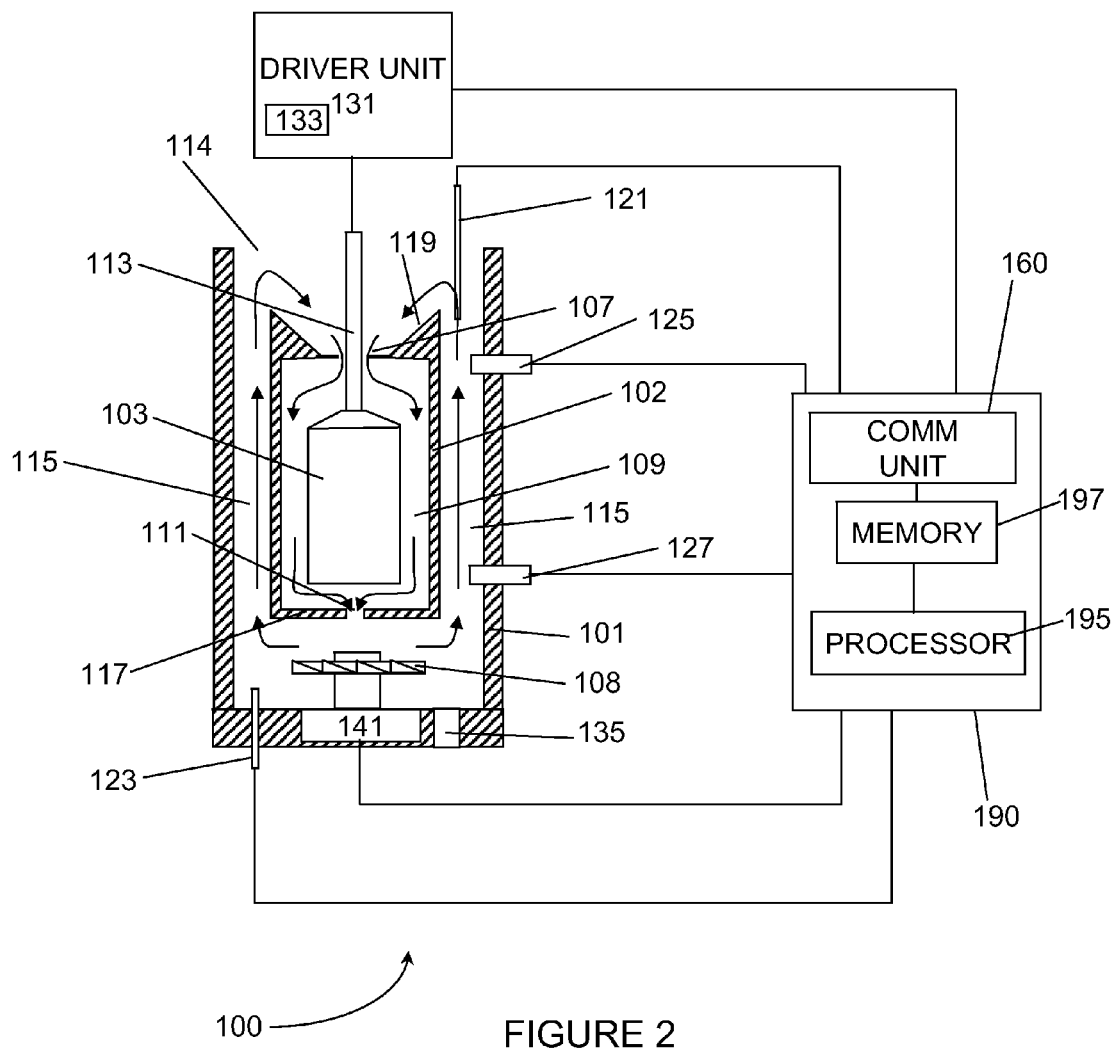
FIG. 2 illustrates an embodiment of a device for testing friction reduction systems with a computer system.

Referring now to FIG. 2, in an embodiment, device 100 may be coupled to a computer 190 for controlling the device and collecting measurements. Computer 190 may comprise various components, such as a processor 195, a memory 197, etc. The processor 195 may comprise one or more micro controllers, microprocessors, etc., that are capable of executing a variety of software components. The memory 197 may comprise various memory portions, where a number of types of data (e.g., internal data, external data instructions, software codes, status data, diagnostic data, testing profiles, operating guidelines, etc.) may be stored. The memory 197 may store various tables or other database content that could be used by the device 100 to implement the override of normal operations. The memory 197 may comprise random access memory (RAM) dynamic random access memory (DRAM), electrically erasable programmable read-only memory (EEPROM), flash memory, hard drives, removable drives, etc.

Computer 190 may also comprise a communication unit 160 capable of facilitating communications between the device 100 and computer 190. In particular, the communication unit 160 is capable of providing transmission and reception of electronic signals to and from an external communications unit. In particular, communication unit 160 may be a wireless device capable of transmitting and receiving signals to and from device 100 without the use of wires.

Sensors (e.g. temperature sensors 121, 123 and/or pressure sensors 125, 127) may be coupled to a computer 190 such that data obtained from sensors may be stored and/or used by computer 190. The computer 190 is capable of receiving internal data and/or external data and generating and delivering signals to device 100. For example, the computer 190 may receive automated and/or manual instructions from a user input, and may send signals to device 100 based on internal calculations, programming, and/or data received from sensors. Thus, computer 190 may be coupled to driver unit 131 for rotating the bob and to motor 141 for rotating the impeller. The computer 190 may also be coupled to a heating and/or cooling element to control the temperature of the sample based upon feedback from the temperature samples. As such, computer 190 may be capable of affecting substantially all functions of the device 100 such as impeller speed, bob speed, temperature of sample, pressure within outer chamber 101, and the like. However, it is also envisioned in some embodiments, speed control of bob 103 and impeller 108 may be adjusted manually by controller units external to computer 190.

In an embodiment, a method of measuring one or more bulk rheological properties of a particle system comprises loading a test material (e.g., a particle laden wellbore servicing fluid) into the outer chamber 101 of the device 100 and sealing the device (e.g., with a lid or topper). Pressure and/or heat may be applied to the sample. For example, the sample may be heated using any suitable methods or devices known to those of skill in the art, thereby causing an increase in pressure and temperature. For example, device 100 may be submerged in an oil bath and/or heating fluids. In another embodiment, outer chamber 101 may incorporate electrical heating elements within its walls to heat the sample. Alternatively, outer wall of outer chamber 101 may comprise a heating jacket. Additionally or alternatively, pressure may be applied directly to the device, for example via a high pressure connection that would inject high pressure gas (e.g., nitrogen) into a head space located at the top of the device above the fluid line of the test sample.

Once the sample is at the appropriate temperature and pressure, mixing impeller 108 may be activated to mix and circulate the sample throughout the device 100. When impeller 108 rotates, it mixes the test sample and forces test sample through circulating gap 115 between inner chamber 102 and outer chamber 101 to inlet 107 of inner chamber 102 as shown by the arrows in FIG. 1. The test sample then enters inner chamber 102 through inlet 107 where test sample cascades down measuring gap 109 as bob 103 rotates. The sample then exits inner chamber 102 through outlet 111 and is re-circulated via the impeller 108.

Bob 103 may be rotated at any suitable angular velocity (i.e. revolutions per minute), which applies a stress to the sample in the annular gap 109. More specifically, bob 103 may be rotated at a rotational speed ranging from about 1 rpm to about 8,000 rpm, alternatively from about 100 rpm to about 8,000 rpm, alternatively from about 300 rpm to about 8,000 rpm. If the stress is sufficient, the fluid will flow in the rotational direction, applying a resulting stress to the bob 103. The stress applied to the outer surface of the bob 103 creates a torque on the bob 103. Torque acting on the outer surface of bob 103 may be measured and recorded as a function of the rotating speed and shearing time. More specifically, torque from the bob 103 may be measured by a torque sensor 133 coupled to bob 103 through shaft 113. Mathematical formulas can be used to transform the dimensions of the bob 103 and inner chamber 102, and the corresponding torque measured by the bob 103 into a set of shear stress and shear rate data. The shear stress and rate of the bob 103 can be calculated by using the equations laid out below. Shear stress may be calculated using the following equation:

$$\tau = \frac{M}{2\pi r_0^2 L}$$

where M is the torque acting on the bob 103, $r_0$ is radius of the bob 103 and L is the length of the bob 103. Shear rate may be determined with the following equation:

$$\dot{\gamma} = \frac{r_0 \Omega_{bob(103)}}{r_0 - r_i}$$

where $r_0$ is radius of the bob 103, $r_i$ is the inner radius of the chamber 102.

Likewise, impeller 108 may be rotated at any suitable rotational speed. Torque acting on the impeller 108 may also be measured and recorded as a function of the rotating speed and shearing time. An additional torque sensor may be coupled to impeller 108 to measure torque of impeller 108. In general, in methods of measuring bulk rheological properties of a particle laden, rotational speed (i.e. angular velocity) of impeller 108 and/or bob 103 are kept constant. However, after bulk rheological properties are measured at a constant shear rate (i.e. impeller 108 speed and bob 103 speed), rotational speed of impeller 108 and/or bob 103 may be increased to measure bulk rheological properties at another different shear rate. The notational speed of impeller 108 and bob 103 may be the same or different from each other.

A typical mode of operation of device 100 is to have impeller 108 and bob 103 rotating simultaneously. Alternatively, device 100 may also be operated with bob 103 in a stationary mode (i.e. non-rotating) and impeller 108 activated (i.e. rotating). For example, after a period of recirculation of the sample fluid in the device the bob may be turned. off. Alternatively, bob 103 may be rotating while impeller 108 may be stationary. For example, after a period of recirculation of the sample fluid within the device the impeller may be turned off. When impeller 108 and bob 103 are rotating simultaneously, they may be rotating in the same or opposite direction from each other.

While a sample is being sheared by bob 103 and/or impeller 108, the temperature of the sample may be monitored at one or more suitable locations in the device. In particular, a temperature sensor 121 may be placed in the annular space 115 between inner chamber 102 and outer chamber 101. In addition, an additional temperature sensor 123 may be placed at the bottom of outer chamber 101 adjacent the impeller 108. Other areas where temperature sensors may be placed include without limitation, adjacent to inlet 107, within annular gap 109, or any surface of outer chamber 101, inner chamber 102, bob 103, or shaft 113.

Embodiments of the disclosed device and methods may be used to measure several different rheological properties including without limitation, viscosity, fluid velocity, shear stress, Taylor instability, rate of gelation and/or crosslinking, or combinations thereof.

In another embodiment, the disclosed device may be used to conduct friction reduction experiments. Specifically, the disclosed device 100 may be used to determine the degradability of a friction reducing agent. As with embodiments of methods to measure bulk rheological properties, a sample may be deposited into the device (e.g., outer chamber 102 and/or inner chamber 101), heated and pressurized to the desired testing temperature and pressure. Impeller 108 may then be turned on and set at a constant rotational speed. Torque and rotational speed of impeller 108 may be continuously monitored. In addition, pressure drop between pressure sensors 125 and 127 may be measured. After sample has been sheared and circulated for a set amount of time, impeller 108 may be stopped and bob 103 may be rotated at a set angular velocity. In one embodiment, bob 103 may be set at a specified angular velocity. Angular velocity of bob 103 may then be decreased and/or increased linearly over time. Torque acting on the outer surface of bob 103 (sensed by torque sensor 133) may be continuously monitored during this decrease and/or increase. Once the experiment is finished, the sample may be drained from outer chamber 101 through an outlet 135 and further analyzed using additional techniques. For example, gas permeation chromatography (GPC) may be used to determine a difference in molecular weight of polymer before and after measurements.

In an exemplary embodiment, the effectiveness of the friction reduction system may be determined be measuring the onset of instability. In particular, the onset of instability may be measured by detecting the onset of Taylor vortices. When the impeller 108 speed exceeds a critical value, the stable flow between rotating cylinders is disrupted and a fluid sample begins to exhibit toroidal instabilities known as Taylor vortices. The Taylor vortices emerge when the centrifugal force becomes large enough to overcome the stabilizing viscous forces. The addition of friction reducing agents (i.e., drag reduction polymers) decreases the intensity and the critical Taylor number of these instabilities which specifies the onset of Taylor vortices. The advantage of drag reduction studies performed in Taylor-Couette flow is that the nature of the instabilities does not vary with time in contrast to chaotic turbulent flow in pipe flow. Thus, the advantages of using the Taylor-Couette approach in studying friction reduction include without limitation, i) ease of use, ii) quick drag reduction characterization; iii) in situ polymer degradation studies, and iv) known techniques of measuring Taylor vortices.

The onset of Taylor vortices for the pure solvent and the polymer solution appears at different angular velocity and the viscosity varies with the polymer concentration. The normalized shear viscosity and normalized speed of rotation are used to unify the results:

$$\eta_N = \eta_T - \eta_{T,0}$$

$$\omega_N = \omega_T - \omega_{T,0}$$

where $\eta_N$ & $\eta_{T,0}$ are viscosity in the Taylor flow region and at the onset of Taylor vortices, respectively. The variables, $\omega_T$ & $\omega_{T,0}$ are the rotational speeds in the Taylor region and at the onset of Taylor vortices. The normalization procedure is applied to account for the polymer induced viscosity change and the Taylor flow domain that is a function of the polymer concentration. This allows direct comparison of the drag reduction effectiveness for different polymer concentrations. The drag reduction effectiveness can be calculated as:

$$DR = 100 - \frac{\eta_N^{solution} - \eta_{N,o}^{solution}}{\eta_N^{solvent} - \eta_{N,o}^{solvent}}$$

With the embodiments of the disclosed device, the concept of Taylor instability may be used to measure the effectiveness of friction reduction. Without being bound by theory, a friction reducing agent may be expected to delay the shift from stability to instability at high rotational speed. Accordingly, the device 100 may be used to determine the effectiveness of a particular friction reducing agent. If a friction reducing agent is degraded during the shearing experiment, then a delay from stability to instability will not be observed. Efficiency of drag reduction can be calculated by using the drag reduction equation given above. Embodiments of the device therefore combine the effects of high shear mixing and Taylor instability together in one simple device. In particular, the effects of shearing on polymer degradation and hence drag reduction effectiveness may be examined in an integrated device.

The device and methods described herein may be used to test any friction reduction system, for example a wellbore servicing fluid or system. Examples of such wellbore servicing fluids include fracturing fluids, spacer fluids, drilling fluids, cementious fluids, acidizing fluids, gravel packing fluids, etc. Furthermore, treatment fluids comprising solid particles often are used in a variety of downhole operations performed in subterranean formations. Such operations include, but are not limited to, production stimulation operations (e.g., hydraulic fracturing) and well completion operations (e.g., gravel packing, cementing, etc).

In an embodiment, the particle laden test fluid is a fracturing fluid. In a hydraulic fracturing operation, a fracturing fluid is placed in a subterranean formation at a rate and pressure sufficient to create or enhance at least one fracture in the formation. The resultant fracture or fractures may be horizontal or vertical, with the latter usually predominating, and with the tendency toward vertical fractures generally increasing with the depth of the formation being fractured. Fracturing fluids generally are viscosified fluids, gels, emulsions, or foams that may comprise particles that often are referred to as "proppant particles." Proppant particles, e.g., sand, are deposited in the fractures and function, inter alia, to maintain the integrity of the fractures, and thereby potentially enhance the conductivity of the formation.

Polymers and other agents have been added to the treatment fluid to help alleviate the stresses that may be caused by increased particle loading. Such polymers are believed to aid in maintaining an even distribution of suspended particles. However, elevated pumping pressure may be required, which may increase the cost and complications associated with the treatment operation. Another known method for combating stresses that may be caused by increased particle loading involves adding a gas phase to the treatment fluid, thereby "foaming" the fluid. The presence of a gas phase is believed to aid in reducing contact between neighboring suspended particles. However, introduction of a gas phase may create an added expense for an operator, and may be problematic when the treatment fluid is to be placed in a high pressure well.

Other types of test fluids include Newtonian and non-Newtonian fluids. To characterize a fluid as one of these, shear stress versus shear rate measurements are made. In Newtonian fluids, the shear stress versus shear rate is a constant called viscosity. Examples of Newtonian fluids are water and certain oils. In non-Newtonian fluids, the shear stress versus shear rate is not constant. Non-Newtonian fluids are classified by their shear stress versus shear rate curves as power law, Bingham, or pseudoplastic fluids. Examples of non-Newtonian fluids include, fracture fluid, gels, drilling muds, and cements. In non-Newtonian fluids, certain rheological properties or characteristics, such as viscosity, shear stress, yield stress, consistency, etc. may be measured.

To further illustrate various illustrative embodiment of the disclosed method and device, the following examples are provided.

EXAMPLE 1

Figure 4:
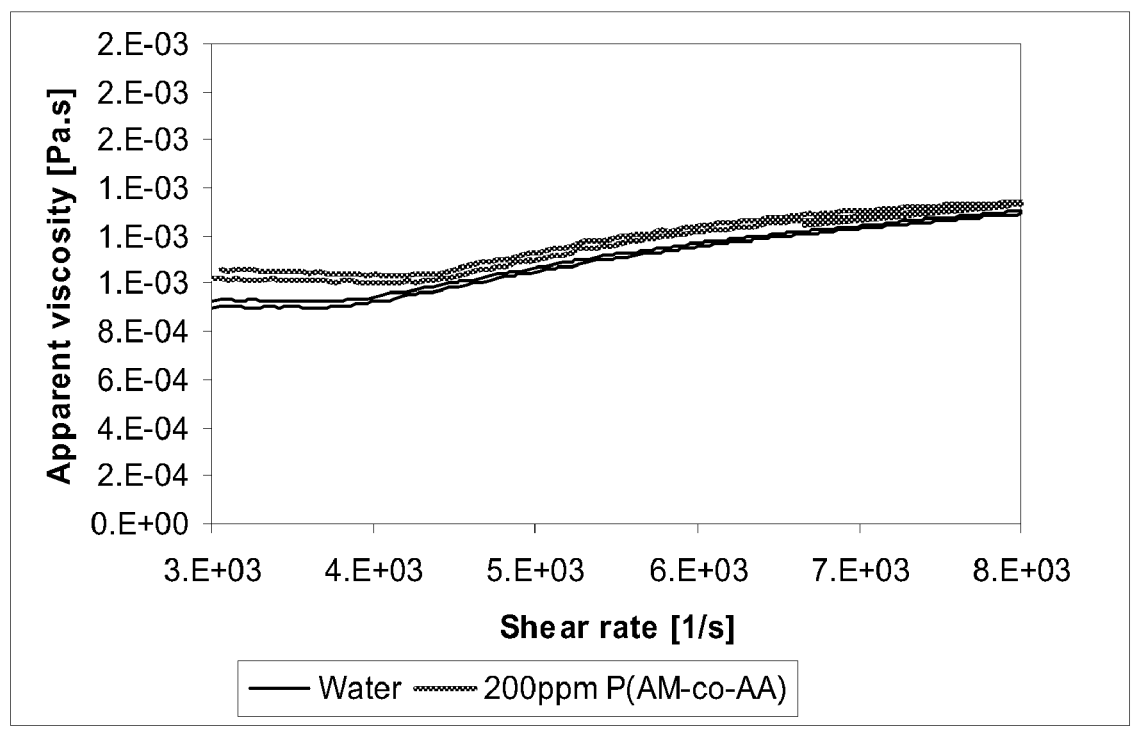
FIG. 4 is a plot of Taylor vortices measurements for water and 200 ppm poly(acrylamide-co-acrylic acid) (P(AM-co-AA)) using an embodiment of the disclosed device.

FIG. 4 shows a typical viscosity-shear rate relationship of water and solution contained with 200 ppm of poly(acrylamide-co-acrylic acid) (P(AM-co-AA)) solutions tested using an embodiment of the disclosed device. The polymer used in this work has the molecular weight [Mw] of $5 \times 10^6$ g/mol. The drag reduction characterization was carried out using the developed device a commercial rheometer (Haake, RS150) equipped with the mixing shield device recently developed in this work. The experiment was carried out without turning the impeller 108, while the bob 103 was ramped up/down in a linear fashion from shear rate of 3000 s$^{-1}$ to 8000 s$^{-1}$ and back from 8000 s$^{-1}$ to 3000 s$^{-1}$ with the acceleration/deceleration rate of 10 s$^{-2}$.

EXAMPLE 2

Figure 5:
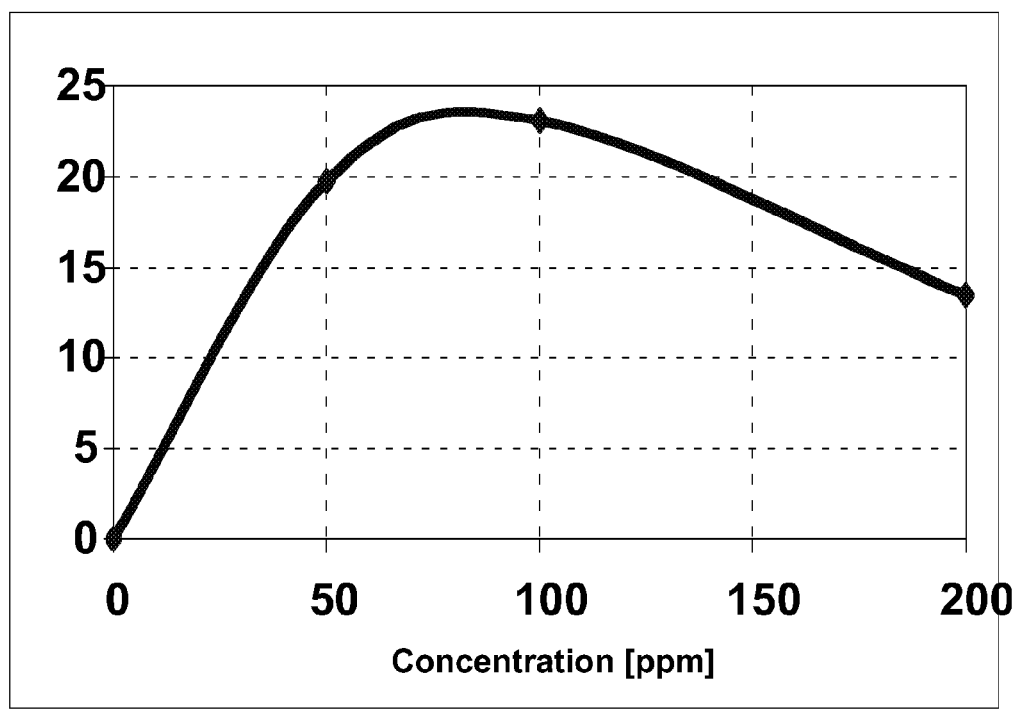
FIG. 5 is a plot of polymer concentration and drag reduction efficiency as measured by an embodiment of the disclosed device.

The device was used to investigate the relationship between polymer concentration and drag reduction efficiency as shown in FIG. 5. FIG. 5 shows the percent drag reduction increasing with increasing polymer concentration until a maximum percentage at a certain polymer concentration value was reached. Additional increases in polymer concentration lead to a small decrease in the drag reduction efficiency. Value of polymer concentration may vary from polymer to polymer.

EXAMPLE 3

Figure 6:
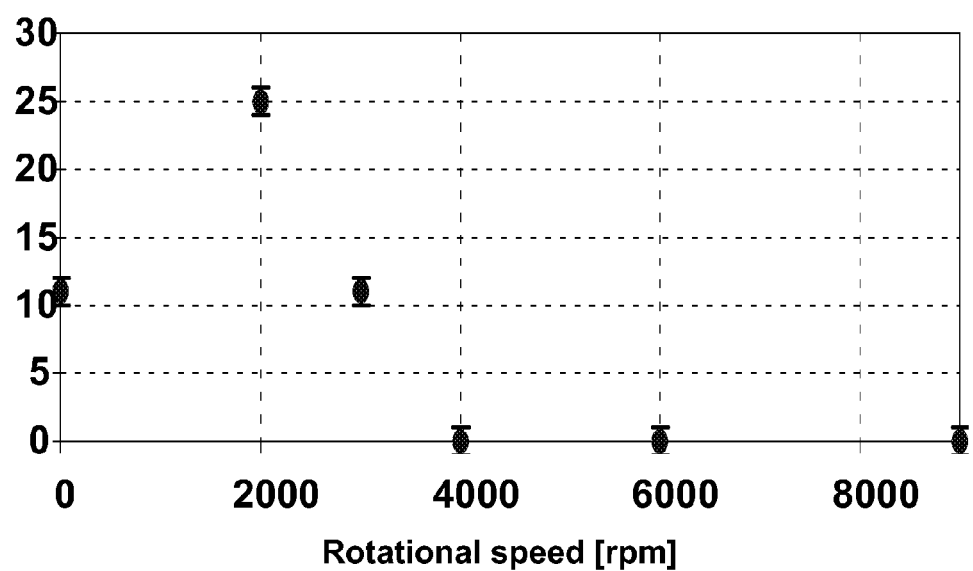
FIG. 6 is a plot showing the effects of mechanical shear on drag reduction efficiency as measured by an embodiment of the disclosed device.

FIG. 6 shows the effect of mixing rate on drag reduction efficiency. In this test the impeller 108 was turned at a fixed. rotational speed of 2000 rpm for fifteen seconds to shout the sample, while the bob 103 was kept stationary during this step. Immediately, the bob 103 was ramped up/down in a linear fashion from shear rate of 3000 s$^{-1}$ to 8000 s$^{-1}$ and back from 8000 s$^{-1}$ to 3000 s$^{-1}$ with the acceleration/deceleration rate of 10 s$^{-2}$ while torque acting on the bob 103 was measured as a function of rotational speed (shear rate), The experiment was conducted at different rotational speed of impeller 108 of 3000, 4000, 6000 and 9000 rpm, A fresh sample was used for each test, There was no change of the procedure used for rotating the bob 103.

The results shown in FIG. 6 revealed that the level of drag reduction increased with increasing the rotational speed of the impeller 108, and fell to zero for high rotational speeds. This result indicated that low rotational speed may improve drag reduction efficiency. However, at high rotational speed, the drag reduction efficiency was reduced. This may due to polymer degradation due to the high mixing rate and consequently loss in drag reduction efficiency of the system.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method of determining one or more bulk theological properties of a friction reduction system comprising:
    a) providing a device comprising an outer chamber, an impeller disposed adjacent the bottom of the outer chamber, an inner chamber fixedly disposed within the outer chamber and in fluid communication with the outer chamber, and a rotatable bob disposed within the inner chamber;
    b) loading the friction reduction system into the device;
    c) circulating the friction reduction system with the impeller so as to circulate the friction reduction system into the inner chamber;
    d) shearing the friction reduction system with the bob as the friction reduction system flows from the outer chamber to the inner chamber;
    e) collecting torque data from one or more torque sensors coupled to the impeller and/or the bob to determine one or more bulk rheological properties of the friction reduction system; and
    f) changing the rotational speed of the impeller and repeating steps (c) through (d) at least once.

2. The method of claim 1 wherein the one or more bulk rheological properties comprises shear stress, viscosity, fluid velocity, or combinations thereof.

3. The method of claim 1 further comprising heating the friction reduction system within the device.

4. The method of claim 1 further comprising pressurizing the friction reduction system within the device, 5. The method of claim 1 further comprising measuring the pressure within the outer chamber.

6. The method of claim 1 further comprising measuring the temperature of the sample at one or more locations within the device.

7. The method of claim 6 wherein the one or more locations comprises inside the outer chamber, inside the inner chamber, or combinations thereof.

8. The method of claim 1 further comprising changing the rotational speed of the bob and repeating steps (c) through (d).

9. The method of claim 1 wherein the friction reduction system comprises a particle laden fluid that is a fracturing fluid.

10. A method of determining onset of instability in a friction reduction system comprising:
    a) providing a device comprising an outer chamber, an impeller disposed adjacent the bottom of outer chamber, an inner chamber fixedly disposed within the outer chamber and in fluid communication with the outer chamber, and a rotatable bob disposed within the inner chamber;
    b) loading the friction reduction system into the device;
    c) shearing the friction reduction system with the impeller so as to circulate the friction reduction system into the inner Chamber;
    d) halting rotation of the impeller and shearing the friction reduction system with the bob as the friction reduction system flows from the outer chamber to the inner chamber; and
    e) decreasing the rotational speed of the bob over time while collecting torque data from a torque sensor coupled to the bob to determine onset of instability in a friction reduction system.

11. The method of claim 10 further comprising heating the friction reduction system within the device.

12. The method of claim 10 further comprising pressurizing the friction reduction system within the device.

13. The method of claim 10 further comprising measuring the pressure within the outer chamber.

14. The method of claim 10 further comprising measuring the temperature of the sample at one or more locations within the device.

15. The method of claim 10 further comprising calculating the Taylor number from the torque data to determine onset of instability.

* * * * *